United States Patent [19]

Gergely et al.

[11] Patent Number: 5,064,656

[45] Date of Patent: Nov. 12, 1991

[54] UNCOATED PHARMACEUTICAL REACTION TABLET

[75] Inventors: Gerhard Gergely; Irmgard Gergely; Thomas Gergely, all of Vienna, Austria

[73] Assignee: Dr. Gergely & Co., Switzerland

[21] Appl. No.: 574,585

[22] Filed: Aug. 28, 1990

[30] Foreign Application Priority Data

Nov. 14, 1989 [CH] Switzerland ............... 4098/89

[51] Int. Cl.$^5$ ............................................. A61K 9/48
[52] U.S. Cl. ................................ 424/463; 424/464; 424/465; 424/466
[58] Field of Search ............... 424/466, 464, 465, 463

[56] References Cited

U.S. PATENT DOCUMENTS

| | | | |
|---|---|---|---|
| 3,136,692 | 6/1964 | Bandelin | 167/57 |
| 4,289,751 | 9/1981 | Windheuser | 424/35 |
| 4,414,198 | 11/1983 | Michaelson | 424/44 |
| 4,555,399 | 11/1985 | Hsiao | 424/35 |
| 4,704,269 | 11/1987 | Korab | 424/44 |
| 4,832,956 | 5/1989 | Gergely et al. | 424/466 |
| 4,888,177 | 12/1989 | Gergely et al. | 424/466 |

FOREIGN PATENT DOCUMENTS

| | | |
|---|---|---|
| 0068191 | 1/1983 | European Pat. Off. . |
| 0207041 | 12/1986 | European Pat. Off. . |
| 0219337 | 4/1987 | European Pat. Off. . |
| 0228164 | 7/1987 | European Pat. Off. . |
| 0257310 | 3/1988 | European Pat. Off. . |
| 1617315 | 1/1970 | Fed. Rep. of Germany . |
| 2020893 | 11/1970 | Fed. Rep. of Germany . |
| 1667895 | 7/1971 | Fed. Rep. of Germany . |
| 2440383 | 3/1976 | Fed. Rep. of Germany . |
| 2546577 | 4/1977 | Fed. Rep. of Germany . |
| 1270781 | 4/1972 | United Kingdom . |
| 2174004 | 10/1986 | United Kingdom . |
| 86/03675 | 7/1986 | World Int. Prop. O. . |
| 8701936 | 4/1987 | World Int. Prop. O. . |

*Primary Examiner*—Thurman K. Page
*Assistant Examiner*—D. Gabrielle Phelan
*Attorney, Agent, or Firm*—Ostrolenk, Faber, Gerb & Soffen

[57] ABSTRACT

An uncoated compressed tablet which is used for the preparation of an orally applicable aqueous suspension or solution of a pharmaceutically active substance contains a mixture of the pharmaceutically active substance, a swelling disintegrant and an effervescent system. The weight ratio of the disintegrant to the effervescent system is from 0.1:1 to 4:1.

22 Claims, No Drawings

UNCOATED PHARMACEUTICAL REACTION TABLET

TECHNICAL FIELD OF THE INVENTION:

The present invention relates to a novel reaction tablet which combines the advantages and eliminates the disadvantages of a common effervescent tablet and a common disintegrating tablet.

BACKGROUND OF THE PRIOR ART

In pharmaceutical technology, there are two known principal systems which effect distribution or dissolution of compressed forms in water, these being the disintegrating tablet on the one hand and the effervescent tablet on the other hand.

In the case of the disintegrating tablet, disintegrants which are added to the tablets cause it to disintegrate after some time in water or in gastric fluid and to release the active substances.

The disintegrating tablets have the disadvantage that their disintegration occurs locally, i.e. they disintegrate at the bottom of the class, and the disintegrated particles remain there, or, owing to the disintegration system, they can give rise to local concentrations in the stomach itself. Disintegrating tablets are therefore not expedient for various active substances.

In addition, disintegrating tablets are difficult to formulate, particularly in the presence of water-soluble substances, since it is known that, after the beginning of disintegration of the tablet, a core remains which does not continue disintegrating or disintegrates to an insufficient extent. Another aspect is acceptance of the flavor of the disintegrating tablet, since certain disintegrants can give rise to an unpleasant flavor.

Another system comprises effervescent tablets in which a reaction between organic acids and bicarbonates or carbonates causes dissolution, carbon dioxide being eliminated from bicarbonates or carbonates; during this process, active substances are distributed or dissolved in a glass of water.

However, the effervescent tablet has the disadvantage that it has to be relatively large and heavy compared with the disintegrating tablet, since the amount of effervescent mixture present must be significantly larger than that of active substance in order to distribute or dissolve the latter or to achieve an appropriate rate.

Attempts have already been made to prepare an effervescent tablet which both disintegrates and effervesces. Such a tablet, which consists of two layers, namely an effervescent layer and a disintegrating tablet, has been disclosed by U.S. Pat. No. 4,832,956. However, this system has the disadvantages that it still requires a large amount of effervescent constituents and nevertheless fails to provide particularly rapid distribution because the effervescent layer becomes lighter owing to the gas formation in the water and the tablet therefore turns so that the effervescent layer faces upward and dissolves more rapidly than the lower disintegrating tablet layer, the disintegrating particles then falling to the bottom of the glass. Furthermore, a two-layer tablet press is required for this purpose, which in turn means greater technical complexity and is therefore uneconomical from the point of view of production technology.

It was previously believed that the components of the two systems would interfere with one another.

Disintegrants in a tablet, for example, starch, microcellulose or crosslinked polyvinylpolypyrrolidone, function all the poorer the more water-soluble the accompanying substances of the tablet. This is due to the fact that the water solubility of the accompanying substances or active substances causes the capillaries of the tablet and of the disintegrant to be blocked, and the resulting concentrated solutions prevent disintegration.

Thus, if an effervescent tablet containing relatively large amounts of disintegrants is prepared, the disintegrant does not function nor does the tablet effervesce, and compressed forms which take several minutes to dissolve are formed.

This also applies to pharmaceutical formulations according to Brit. Pat. 1093286 or U.S. Pat. No. 4289751.

In the Brit. Pat., mixtures of an effervescent system with a disintegrant are filled into a gelatine capsule which is resistant to gastric fluid, swells in the duodenum and bursts owing to the internal evolution of gas. Such a capsule exhibits virtually no solubility in water; if the mixture, for example from Example 2 stated there, is pressed to give an uncoated tablet, only isolated gas bubbles are evolved when the tablet is introduced into water; the tablet dissolves very slowly and takes as long as 20 to 30 minutes.

The U.S. Patent, too, describes a coated tablet which is resistant to gastric fluid and is intended to release its active substance only in the intestine. The combination of an effervescent system with a disintegrant is intended here to achieve better distribution in the intestine; whether the time for disintegration or for dissolution or for the effervescent effect in the intestine is 30 seconds or 30 minutes plays absolutely no role here. In fact, the tablets described there require 120 seconds or more for dissolution, even without a coating. This is certainly partly due to the microcrystalline cellulose which, according to claim 9, is also used there as a dry binder and which, for the purposes of the present invention described below, is not to be regarded as a disintegrant, as will be shown further below in Example 17.

It is the object of the invention to develop a tablet which combines the essential advantages of both the disintegrating tablet and the effervescent tablet in one system.

SUMMARY OF THE INVENTION

The reaction tablet of the invention contains at least one active substance, at least one disintegrant and at least one constituent which eliminates a gas on reaction with another tablet constituent (both constituents together are referred to below as "reactants"), as a mixture with one another, in particular in a weight ratio of disintegrant to reactants of 0.1 : 1 to 4 : 1, preferably 0.3 : 1 to 2 : 1. Expediently, at least one reactant goes into solution more slowly and/or reacts more slowly with the other reactant or reactants than the disintegrant or disintegrants absorbs or absorb water. In particular, the disintegrants and reactants together account for 25 to 75, preferably 33 to 60, percent by weight of the total tablet.

If the reactants composing the effervescent system are a carbonate and/or bicarbonate e.g. an alkali or alkaline earth metal carbonate and/or bloarbonabe and an edible organic acid, preferably at least 50% of the carbonate and/or bicarbonate have a particle size of more than 0.05 mm, preferably more than 0.1 mm, at least 15% of the acid reactant of the effervescent system should have a particle size of between 0.2 and 0.5 mm if it is L-tartaric acid, 0.05 to 0.2 mm if it is monosodium citrate and/or adipic acid, less than 0.1 mm if it is fumaric acid and more than 0.3 mm if it is citric acid.

Particles of at least one reactant may be coated with a slowly soluble physiologically acceptable substance, such as a long-chain polyvinylpyrrolidone or polyethylene glycol.

The disintegrating agent is best selected from the group consisting of nonsoluble ones, such as crosslinked polyvinylpolypyrrolidone and/or starch, preferably both mixed in a ratio of 1:0.25 to 1 : 3.0.

The disintegrating agent, especially if it is starch, may be charged with 1 to 20, preferably 3 to 10, % by weight of a physiologically acceptable compound which is soluble in a solvent which does not swell the disintegrating agent, for example an edible organic acid or a long-chain noncrosslinked polyvinylpyrrolidone. The disintegrant may be anchored to the surface of the particles of at least one of the reactants.

The reaction tablet of the invention has the advantage of the low weight of a disintegrating tablet but improves its core disintegration and hence the solubility or suspension of the active substance, because the disintegrating particles are fluidized despite a substantially smaller amount of gas-evolving constituents and hence an effervescent effect which is much smaller compared with a conventional effervescent tablet. The tablet according to the invention is referred to below as a reaction tablet.

The invention is applicable to virtually all pharmaceutical active substances which have an acceptable taste in solution or suspension. Because such a small amount of disintegrant and gas-evolving reactants is sufficient, larger amounts of flavor-improving excipients can be incorporated in the formulation, facilitating formulation in many cases.

In a suitable formulation, oxygen-evolving systems, such as, for example, those containing potassium hydrogen persulfate, in the composition according to the invention, may also be used, particularly for purifying tablets.

Particularly when the effervescent effect is furthermore greatly delayed by suitable measures so that disintegration or effervescence takes place in two separate processes or processes which at least only partially overlap one another, a particularly rapidly disintegrating and effervescing tablet which suspends or dissolves the active substances is obtained. This is achieved, for example, by selecting a very rapid disintegrant and/or an effervescent system which consists of relatively sparingly soluble and/or slowly reacting constituents, or of constituents which have been rendered relatively sparingly soluble or less reactive by pharmaceutical methods.

For the purposes of the present invention, a disintegrant is any substance which absorbs water and conveys it very rapidly to the interior of the tablet before the gas evolving reaction begins, even if this substance itself does not act as a disintegrant in the conventional sense.

The simplest model is, for example, a disintegrating effervescent tablet which contains crosslinked, highly polymeric polyvinylpolypyrrolidone as the disintegrant on the one hand and a mixture of coarsely crystalline tartaric acid and coarsely crystalline sodium bicarbonate as the effervescent system on the other hand. A tablet produced in this manner disintegrates within a few seconds; the reactive effervescent constituents are initially liberated by the rapid disintegration and then react vigorously and also within a few seconds, in the same way as an instant effervescent tablet.

If, on the other hand, the active substance is compressed, for example with a small amount, according to the invention, of effervescent mixture alone, an effervescent tablet of this type then requires about 3 to 4 minutes to dissolve since, owing to the slow reaction, it scarcely effervesces at all and is very sluggish. However, if an effervescent tablet of this type is even only partly disintegrated by the disintegrant before the reaction, the liberated acids and bicarbonates/carbonates react relatively vigorously and fluidize the disintegrated tablet particles, so that dissolution and/or uniform suspension occurs rapidly.

Remarkably, it is known that disintegrants initially disintegrate the tablet at the outer periphery, after which, however, a smaller or larger core remains and no longer disintegrates by itself or disintegrates only very slowly. If a dimensioned effervescent system having the composition according to the invention is added to such a system, the tablet likewise initially begins to disintegrate into particles at its periphery. However, since the otherwise poorly disintegrating core has also become wet with water, the corresponding effervescent system can attack and can completely disintegrate the tablet with pronounced fluidization.

In this way, it is possible to obtain the following decisive advantages:

The weight of the reaction tablets according to the invention can be dramatically reduced compared with conventional effervescent tablets so that, for example by suitable choice of the disintegrating effervescent system, it is also possible to take the tablet directly without water;

The amount of water required for intake can likewise be greatly reduced compared with conventional effervescent tablets, for example from the previous amount of 100-150 ml to 20-50 ml;

In conventional disintegrating tablets, certain flavorings, accompanying substances or aromas interfere with the disintegration process; in the reaction tablet according to the invention, it is possible to incorporate aromas, sugar-like sweeteners, etc. without interfering with the disintegration/effervescence process, quite apart from the fact that substantially better aromatization is possible through the addition of organic acids and the choice of an appropriately low pH.

In the formulation of such tablets, it is possible to manage with surprisingly small amounts of accompanying substances.

DETAILED DESCRIPTION OF THE INVENTION

A few easily reproducible Examples (No. 1 to 9) are described below to explain the System. In each case, the stated amounts (in mg) of the individual constituents are mixed and the mixture is pressed to give tablets. The abbreviations have the following meanings:

PVPP: Crosslinked, high molecular weight polyvinylpolypyrrolidone

Lact.: Tablettose, i.e. directly compressible lactose of particle size 0.05-0.2 mm TA: Tartaric acid (coarse: 0.3-0.8 mm)

CA FG: Citric acid, fine grit (0.1-0.5 mm) Rice starch <0.1 mm.

|  | Example No. | | | | | |
| --- | --- | --- | --- | --- | --- | --- |
|  | 1 | 2 | 3 | 4 | 5 | 6 |
| Disintegrant | 50 PVPP | — | 50 PVPP | 100 rice starch | — | 100 rice starch |
| Basic effervescent constituent | — | 50 NaHCO$_3$ | 50 NaHCO$_3$ | — | 50 NaHCO$_3$ | 50 NaHCO$_3$ |
| Acidic effervescent constituent | — | 50 TA coarse | 50 TA coarse | — | 50 TA coarse | 50 TA coarse |
| Filler | 300 Lact. | 300 Lact. | 300 Lact. | 300 Lact. | 300 Lact. | 300 Lact. |
| Dissolution time in sec | 35 | 75 | 20–30 | 2–3 min | Unusable | 30–45 sec |
| Comments | Core remains behind | Very little gas evolved |  |  | Core remains behind | Very little gas evolved |

|  | Example No. | | |
| --- | --- | --- | --- |
|  | 7 | 8 | 9 |
| Disintegrant | 100 rice starch | 100 rice starch | 100 rice starch |
| Basic effervescent constituent | 40 NaHCO$_3$ (0.1–0.25 mm) | 40 NaHCO$_3$ (0.2–0.5 mm) | 20 NaHCO$_3$ 0.2–0.5 mm) |
| Acidic effervescent constituent | 60 fumaric acid | 60 adipic acid | 60 CA FG |
| Filler | 300 Lact. | 300 Lact. | 300 Lact. |
| Dissolution time in sec | 45 | 50 | 90 |

In all systems European Patent Application 90121562.4, it is very easy to observe that initial disintegration caused by the disintegrant immediately changes into instant effervescence of the disintegrated products, which in turn disintegrate the core which would otherwise remain.

Replacement of lactose by granulated mannitol is just as easy to demonstrate. Here too, virtually identical values are obtained.

It is possible, for example, to formulate a tablet containing 200 mg of paracetamol as a 400 mg tablet by merely adding 100 mg of PvPP, 50 mg of coarsely crystalline tartaric acid and 50 mg of coarse sodium bicarbonate (0.1–0.2 mm) to the 200 mg of paracetamol. Even the use of sodium carbonate instead of sodium bicarbonate still gives quite rapidly dissolving tablets, such systems also having the advantage that they achieve an excellent shelf life owing to the stable and nonhygroscopic sodium carbonate.

Instead of PVPP, starch, in particular rice starch, can also advantageously be used as a disintegrant in delayed-action effervescent combinations in many cases, in particular modified starch according to Patent . . . (Patent Application of the same day: "Modified starch and processes for its preparation"), for the reasons stated there; the description given there is hereby incorporated by reference herein.

Since PVPP is water-insoluble and is also difficult to suspend owing to the relatively large particle size, it may be advantageous to use mixtures of disintegrants, a particularly advantageous ratio being, for example, 1 part by weight of PVPP and 0.5 parts by weight of starch.

Rice starch having a low water content has proven particularly advantageous, but other starches, such as cornstarch, may also be used; combinations of starch with other disintegrants, such as PVPP or microcellulose, also give the desired disintegration times since they cause rapid penetration of the tablet by water and accordingly rapid disintegration before the beginning of the effervescence reaction.

Although tartaric acid in somewhat coarser crystalline form, together with the stable, very slowly reacting sodium carbonate, is suitable, in particular other acids which react slowly can also be successfully used. For example, the very finely crystalline fumaric acid is generally very suitable since it dissolves very slowly and reacts slowly. With fumaric acid, it is also possible to prepare systems in which the disintegration is not quite so rapid, owing to somewhat higher water solubility of the active substance. In general, the following rule applies the more watersoluble the active substance, the slower must the effervescent system be.

It is also possible to obtain a certain optimum pH for the individual active substances with this system.

Furthermore, only small shifts between acids and alkalis are required to obtain the desired final pH; the strong buffer effect of conventional, heavy effervescent tablets plays an important role here.

Completely unexpectedly, the ratio of disintegrant to effervescent mixture on the one hand and that of both together to the accompanying tablet mass not only can be relatively small but even should be so. If, for example, the amount of disintegrant or the amount of effervescent mixture is increased, the total system does not become faster, as would be expected, but significantly slower. This is a very important situation with regard to medication It has been necessary to date to accept a relatively large amount of sodium and/or potassium for effervescent tablets. For health reasons, however, both are undesirable in large doses. Furthermore, potassium has a soapy taste. However, it is now possible dramatically to reduce the previously required amount of these substances per tablet.

The system also has important advantages with regard to the stability of the active substance. Since, owing to the coarse structure and the low solubility of the substances used, the mechanical contact with the active substances is small and furthermore the reactivity of the substances has been intentionally reduced, the stability of the active substances to adverse effects of alkaline or acidic constituents has been very greatly improved. In particular, the stability to moisture and water vapor is significantly improved compared with normal effervescent tablets, since the accompanying disintegrant, such as, for example, starch, reduces the sensitivity to atmospheric humidity.

The more highly soluble the constituents of the tablet, whether active ingredients, excipients or reactants, the more rapidly they go into solution (under otherwise identical conditions) and inhibit the action of the disintegrant. For example, acetylcisteine, vitamin C or caffeine have, however, been found to have no adverse effect on water transport into the interior of the tablet. On the other hand, various sugars as well as steviosides as sweeteners are too highly soluble and thus delay tablet disintegration. It would therefore be necessary to render them more slowly soluble by a suitable coating or to select a particularly large crystal form or compounds which dissolve correspondingly more slowly. Suitable acidic constituents of the effervescent system or suitable reactants which evolve gas with carbonates are the following edible organic acids, in order of decreasing solubility: citric acid monohydrate anhydrous citric acid - L-tartaric acid - malic acid adipic acid - fumaric acid. Acidic citrates, such as, for example, monosodium citrate, can also be used as an effervescent constituent.

However, the types of constituents overlap one another in this sequence. For example, citric acid monohydrate, which is more highly soluble and dissolves more rapidly in fact dissolves more slowly than anhydrous citric acid because it only goes into solution with absorption of energy (endothermic) whereas anhydrous citric acid - before it goes into solution - first has to form a hydrate, which, however, takes place with release of energy (exothermic), the dissolution process being accelerated by the local generation of heat.

While the less stable tartaric acid is more suitable than the more soluble citric acid for achieving the object according to the invention, at any rate according to the above sequence, the particle size may reverse the situation: a coarsely crystalline citric acid dissolves more slowly than a finely powdered tartaric acid.

The situation is similar when the effervescent mixture contains the carbonate; the suitable compounds are as follows, in order of decreasing solubility: sodium glycine carbonate, potassium carbonate, potassium bicarbonate, sodium carbonate (anhydrous), sodium bicarbonate. The first two are much too rapidly soluble (furthermore, in contrast to sodium carbonate, potassium carbonate need not incorporate any water of crystallization), to be preferred according to the invention.

Another criteria is the rate of the reaction of the effervescent constituents with one another: the slower the reaction, the better can the disintegrant initially display its effect. The reaction rate for the two reactants in turn is dependent on the one hand on their solubility and on the other hand on the particular pK. While citric acid itself has a pK of less than 3, monosodium citrate has a pK of more than 4 and therefore reacts more slowly with the carbonate. According to the invention, it is therefore more suitable than citric acid as the acidic component of an effervescent mixture.

The next step would lead to disodium citrate; however, this is once again superposed by the fact that this compound reacts too slowly, so that the effervescent effect begins too late with respect to tablet disintegration, or the tablet disintegrates too slowly, if the reactants only go into solution initially and prevent swelling of further disintegrant particles before they begin to react and hence to effervesce and to mix the solution or suspension.

The dissolution and/or reaction rate of at least one reactant may furthermore be slowed down by wetting the individual particles with a solution - for example an alcoholic solution - of a slowly dissolving coating material and drying them. For example, polyethylene glycol or relatively long-chain, unbranched polyvinylpyrrolidone (PVP) is suitable for this purpose. They then also have a better shelf life.

In principle, however, the disintegrant itself in the mixture acts as a disintegrant which separates the reactants from one another so that they react more slowly with one another, and do so only when the tablet has absorbed water throughout (as far as possible like a sponge). Evolution of gas then begins simultaneously in the whole tablet; the reaction tablet according to the invention is not slowly disintegrated like a conventional effervescent tablet from the surface inward.

A few examples of tablets according to the invention are described below, various acidic reactants and various substances which evolve carbon dioxide being used. 5 mg of saccharin and 5 mg of aroma were first added to 50 mg of each of the two effervescent constituents ($NaHCO_3$ with 75% 0.1–0.25 mm and coarse tartaric acid). 100 mg of disintegrant and 200 mg of ibuprofen (<0.6 mm) were then added to this "base" and the mixture was pressed to give tablets (12 mm diameter, hardness about 6).

An important criterion is the ratio of disintegrant to effervescent mixture. If this is less than about 1 4, the dissolution (disintegration) times, for example for ibuprofen, are as a rule more than one minute and are therefore useless. If the ratio is more than 4 1, the tablet disintegrates rapidly but the effervescent effect is so small that rapid dissolution or distribution or suspension of the active substance in the solution does not occur.

EXAMPLES 10 to 14

Variation of the ratio of disintegrant to reactants and of the sum thereof to the active substance (each tablet contains 200 mg of Ibuprofen (<0.6 mm); PVPP as disintegrant; 1 : 1 anhydrous $Na_2CO_3$/tartaric acid (>0.3 mm) as reactants) per tablet with constant or increasing tablet weight:

|  | Example No. | | | | | |
| --- | --- | --- | --- | --- | --- | --- |
|  | 10 | 11 | 12 | 12a | 13 | 14 |
| Disintegrant (mg) | 60 | 150 | 200 | 100 | 100 | 100 |
| Reactants (mg) | 240 | 150 | 100 | 100 | 200 | 400 |
| Dissolution time (sec) | 450 | 30 | 20 | 75 | 40 | 180 |

A ratio of disintegrant to reactants of 0.5 (Example 13) through 1 (Examples 11 and 12a) to 2 (Example 12) is suitable; Example 12a is better than Example 11 because the latter has amounts of disintegrant and reactants which are too large compared with the active substance. This effect is reversed in the ratio of disintegrant to reactants of 1 : 4, which is in principle useless, because with 400 mg (Example 14) to 200 mg of active substance the effervescent effect is still better than with only 240 mg (Example 10).

EXAMPLES 15 to 17

Variation of the disintegrant (each tablet contains 200 mg of ibuprofen (<0.6 mm); 100 mg of the effervescent system 1 : 1 $NaHCO_3$ 0.1–0.25 mm/tartaric acid >0.3 mm; and 100 mg of disintegrant):

|  | Example No. | | |
| --- | --- | --- | --- |
|  | 15 | 16 | 17 |
| Disintegrant | PVPP | Rice starch | microcristalline cellulose |
| Dissolution time in sec | 35 | 40 | >120 |
| Comments | Readily suspended | Some core remains behind | Useless |

Rice starch swells somewhat more slowly than PVPP; the microcrystalline cellulose (Avicel) evidently swells too slowly.

EXAMPLES 18 to 20

Variation of the basic effervescent constituent (each tablet contains 200 mg of ibuprofen (<0.6 mm) and 100 mg of PVPP):

|  | Example No. | | |
| --- | --- | --- | --- |
|  | 18 | 19 | 20 |
| Alkaline effervescent constituent | 40 $KHCO_3$ | 50 $Na_2CO_3$ | 50 $K_2CO_3$ |
| Acidic effervescent constituent | 60 TA coarse | 50 TA coarse | 50 TA coarse |
| Dissolution time in sec | 35 | 20 | >120 |

Potassium carbonate evidently dissolves too rapidly.

EXAMPLES 21 to 26

Variation of the acidic effervescent const (100 mg of PVPP, 50 mg of $NaHCO_3$ 0.1–0.25 mm, 200 mg of ibuprofen per tablet):

|  | Example No. | | |
| --- | --- | --- | --- |
|  | 21 | 22 | 23 |
| Acidic effervescent constituent | 50 TA coarse | 50 adipic acid | 50 fumaric acid |
| Dissolution time in sec | 35 | 25 | 15 |

(100 mg of rice starch, 300 mg of Lact. per tablet):

|  | Example No. | | |
| --- | --- | --- | --- |
|  | 24 | 25 | 26 |
| Alkaline effervescent constituent | 40 $NaHCO_3$ | 40 $NaHCO_3$ | 40 $NaHCO_3$ |
| Acidic effervescent constituent | 60 fumaric acid | 60 adipic acid | 60 citrate |
| Dissolution time in sec | 45 | 40 | 50 |

Replacing rice starch by PVPP in Examples 24 to 26 reduces the disintegration times. The difference between rice starch and PVPP is that the rice starch is very readily suspended in water whereas the waterinsoluble PVPP produces insoluble residues on the bottom.

Another criterion is the solubility, as well as the shape and particle size of the active substance and of any other additives. Insoluble or sparingly soluble active substances (for example profens, antibiotics, paracetamol) do not adversely affect the reaction sequence of a tablet, desired according to the invention, by going into solution, but—particularly when they are very finely powdered, in which form such active substances are frequently used—may coat the other constituents and thus inhibit their dissolution and/or reaction (possibly to an undesirably great extent). In this case, such inhibition must be counteracted in formulation by means of suitable measures, which would have an absolutely negative effect on more readily and/or more rapidly soluble active substances (for example acetylsalicylic acid, vitamin C, caffeine).

From the above description, it can be seen that the potential variations of the system are infinite. A limited number of examples with a very wide range of active substances and the results thereof have therefore been summarized in Tables:

In the following Examples, 100 mg of PVPP, 50 mg of anhydrous $Na_2CO_3$, 50 mg of coarse tartaric acid, saccharin and aroma are mixed with 200 mg of active substance and the mixture is pressed to give a tablet.

EXAMPLES 27 to 32

Variation of the active substance

|  | Example No. | | | | | |
| --- | --- | --- | --- | --- | --- | --- |
|  | 27 | 28 | 29 | 30 | 31 | 32 |
| Active substance | Ibuprofen | Acetylsalicylic acid | Paracetamol | Propanolol | Acetylcysteine | Vitamin C |
| Dissolution time in sec | 20 | 50 | 15 | 30 | 20 | 20 |

As already mentioned, the particle size of the constituents of the effervescent mixture is also important and has an effect. Under otherwise identical conditions, a tablet which contains only tartaric acid crystals larger than 0.8 mm dissolves in 20 seconds; in the case of particle sizes of less than 0.2 mm, this time increases to more than one minute and the dissolution behavior is thus unsuitable. The reason for this on the one hand is that the very small tartaric acid crystals dissolve more rapidly; the tartaric acid solution blocks the pores of the disintegrant, which therefore cannot swell so readily. On the other hand, finer particles give a more highly compressed tablet into which water can penetrate only to a smaller extent (or more slowly), water being necessary both for the swelling effect and for the effervescent effect.

EXAMPLES 33 to 37

Effect of particle size (200 mg of ibuprofen, 100 mg of PVPP, 50 mg of $Na_2CO_3$ and 50 mg of tartaric acid per tablet):

|  | Example No. | | | | |
| --- | --- | --- | --- | --- | --- |
|  | 33 | 34 | 35 | 36 | 37 |
| Particle size of tartaric acid in mm | powder | <0.2 | 0.2–0.4 | 0.6–0.8 | 0.8–1.2 |
| Dissolution time in sec | >300 | 130 | 55 | 25 | 20 |

By selecting the type and amount of disintegrant, of the acids and of the $CO_2$-evolving constituents, the optimum result can be found for each active substance in a relatively short time and in a limited number of experiments.

Furthermore, sparingly soluble acids may have a finer structure while more readily soluble acids and constituents must be present in coarser form in order to achieve disintegration times of less than one minute. Consequently, even when more readily soluble active substances are used, more sparingly soluble acids having a smaller particle size are preferable for achieving better content uniformity since, for example, tartaric acid having a large particle size may give rise to difficulties in achieving distribution of the active substance.

EXAMPLE 38

The dissolution time (in sec) of tablets of, in each case, a different active substance mixed with, in each case, a different disintegrant/reactant combination is listed in the Table below. PVPP denotes crosslinked polyvinylpolypyrrolidone TA denotes coarse tartaric acid (0.3–0.5 mm) Avicel denotes microcellulose NBC denotes coarse sodium bicarbonate (75% 0.1–0.25 mm)

To obtain a better overview and for better comparability, some of the above-mentioned Examples are also contained in this Table:

local concentrations cannot occur in the stomach because the effervescent effect ensures distribution and, on the other hand, distribution occurs before intake when the tablet is taken in a glass of water.

EXAMPLE 39

According to the invention, it is also possible to produce a reaction tablet containing the active substance beta-carotene which to date has been difficult to incorporate in an effervescent tablet, owing to foam formation and dispersion.

| | |
|---|---|
| 150 | parts of beta-carotene (10% water-dispersible, 0.1 mm) |
| 150 | parts of rice starch (charged with 60 parts of tartaric acid |
| 275 | parts of granulated mannitol, particle size 0.2 mm |
| 200 | parts of crystalline tartaric acid |
| 150 | parts of anhydrous sodium carbonate |
| 5 | parts of saccharin |
| 20 | parts of dry aroma |
| 1000 | parts are compressed to give a tablet which has a hardness of 7 kp and a dissolution or dispersion time of 60 sec. |

EXAMPLE 40

| | Ibu-profen <0.6 mm 200 mg | Acetyl-salicylic acid 200 mg | Para-cetamol cryst. 200 mg | Propra-nolol. HCl 20 mg | Acetyl-cisteine 0.3–0.5 mm 200 mg | Vitamin C 200 mg |
|---|---|---|---|---|---|---|
| 100 PVPP 50 NBC 50 TA | 35 | 20 | 20 | 35 | 20 | 15 |
| 100 rice starch 50 NBC 50 TA | 40 | 45 | 30 | 70 | 30 | 50 |
| 100 Avicel 50 NBC 50 TA | all much too slow | | | 180 | >240 | 180 |
| 100 PVPP 50 $Na_2CO_3$ 50 TA | 20 | 50 | 15 | 30 | 20 | 20 |
| 100 PVPP 50 $K_2CO_3$ 50 TA | all much too slow | | | | | |
| 100 PVPP 50 NBC 50 fumaric acid | 15 | 20–25 | 20–25 | 20–25 | 20–25 | 20–25 |
| 100 PVPP 50 NBC 50 adipic acid | 25 | 40 | 20 | 30 | 25 | 45 |
| 100 rice starch 50 $Na_2CO_3$ 50 fumaric acid | 60 | 90 | 15 | 150 | 60 | 70 |

The stated Examples clearly show that, by simply altering the relationships and compositions, dissolution times of between 15 and 90 seconds can be obtained, depending on the active substance.

According to the invention, it is also therefore very easy to program the times for the disintegrating effervescent tablet in such a way that the tablet can also be taken directly without water, the tablet disintegrating without effervescence only after it has been swallowed and enters the stomach. Such tablets can therefore be used in both ways, by either swallowing them directly or allowing them to disintegrate with effervescence in a very small amount of water. Thus, the patient himself can choose which mode of administration he prefers. Both modes of administration are advantageous since

| | |
|---|---|
| 40 | mg of propanolol HCl |
| 30 | mg of rice starch |
| 93 | mg of PVPP |
| 220 | mg of tablettose |
| 108 | mg of sodium carbonate |
| 93 | mg of fumaric acid |
| 130 | mg of tartaric acid (0.3–0.5 mm) |
| 20 | mg of aroma |
| 7 | mg of saccharin |
| 746 | mg are compressed to give a tablet which dissolves in 50 ml of water in the course of about 40 seconds. |

EXAMPLE 41

| | |
|---|---|
| 200 mg | of ibuprofen <0.3 mm |
| 2 mg | of Aerosil |
| 200 mg | of rice starch |
| 50 mg | of PVPP |
| 318 mg | of tablettose |
| 200 mg | of potassium bicarbonate |
| 280 mg | of crystalline tartaric acid |
| 20 mg | of saccharin |
| 40 mg | of lemon aroma |
| 1310 mg | are compressed to give a tablet which dissolves in 50 ml of water in the course of about 60 sec. |

EXAMPLE 42

| | |
|---|---|
| 250 mg | of amoxicillin trihydrate |
| 100 mg | of PVPP |
| 50 mg | of MpS 04/DA |
| 50 mg | of potassium bicarbonate |
| 70 mg | of adipic acid |
| 10 mg | of saccharin Na |
| 20 mg | of orange aroma |
| 550 mg | are compressed to give a tablet which dissolves in 50 ml of water in the course of 50-60 seconds. |

EXAMPLE 43

| | |
|---|---|
| 200 g | of acetylcysteine |
| 50 mg | of rice starch |
| 20 mg | of tablettose, about 0.2 mm particle size |
| 110 mg | of calcium carbonate powder |
| 50 mg | of fumaric acid, smaller than 0.05 mm |
| 10 mg | of saccharin Na |
| 60 mg | of "cassis" aroma |
| 200 mg | of granulated mannitol Ro (0.1–0.2 mm) |
| 700 mg | are compressed to give a tablet which - depending on the tablet hardness - dissolves in 50 ml of water in the course of 60 to 70 seconds. |

According to a further embodiment of the invention, the disintegrant is anchored to one of the two reactants with the aid of instant technology (carrier coating). For this purpose, the carrier, for example the acid crystal, is first moistened with a solution, the disintegrant is applied in the moist state and drying is then carried out in vacuo, in particular under mild conditions, so that the coating does not fall off during the movements necessary for drying.

In principle, each of the two reactants can be coated with the disintegrant; however, it has proven advantageous to coat the acid component - both from the point of view of the particle structure and because drying is easier. To moisten the acid component or to bind the disintegrant, it is possible to use both a neutral substance, such as, for example, starch syrup or polyvinylpyrrolidone, in an alcoholic or alcoholic aqueous solution, and an alcoholic or alcoholic aqueous tartaric acid solution (the latter where tartaric acid is the acid component), in which case the subsequent disintegrant, i.e. for example starch, does of course absorb tartaric acid. If such a carrier-coated tartaric acid is then mixed with bicarbonates, effervescence occurs immediately and does not have the usual effect that the tablet first disintegrates and then effervesces. Nevertheless, the initial effervescence is however so weak that substantial disintegration occurs during the effervescence, i.e. effervescence and disintegration occur simultaneously. If, on the other hand, a neutral substance, such as, for example, glucose syrup, is used for binding the disintegrant to the acid, another phenomenon is observed: the tablet disintegrates first and effervescence occurs after exposure of the coated tartaric acid.

With the system according to the invention, it is even possible (depending on the active substance) to use a citric acid coated in this manner as the acidic reactant, since the coating, for example of starch, reduces the reactivity with the alkaline reactant and the principle of delayed reaction is thus maintained.

EXAMPLE 44

In each of the compositions stated below, the base component (carrier) is heated to 60° C. in a drum while stirring, after which the binder solution is added and is distributed uniformly over the surface of the base component. The disintegrant is then added and is distributed uniformly over the granules. These are then dried in vacuo at 70° C. until the weight remains constant and then are discharged onto a sieve, mixed with the desired remaining constituents and compressed to give tablets:

| | | |
|---|---|---|
| a. | Base component | 78% of citric acid, fine grit |
| | Binder | 2% of PVP K30 dissolved in 3.5% alcohol |
| | Disintegrant | 20% of rice starch |
| | | 100% |
| b. | Base component | 90% of citric acid, fine grit |
| | Binder | 1% of PVP K30 dissolved in 4% alcohol |
| | Disintegrant | 9% of PVPP (Polyplasdone XL) |
| | | 100% |
| c. | Base component | 73% of tartaric acid, fine grit |
| | Binder | 2% of tartaric acid in a 50% 1:1 water/alcohol solution |
| | Disintegrant | 25% of rice starch |
| | | 100% |
| d. | Base component | 73% of tartaric acid, fine grit |
| | Binder | 2% of tartaric acid in a 50% 1:1 water/alcohol solution |
| | Disintegrant | 25% of PVPP (Polyplasdone XL) |
| | | 100% |
| E. | Base component | 77% of tartaric acid, fine grit |
| | Binder | 3% of starch syrup dissolved in 1.5% of water |
| | Disintegrant | 20% of rice starch |
| | | 100% |
| f. | Base component | 77% of tartaric acid, fine grit |
| | Binder | 3% of starch syrup, dissolved in 1.5% of water |
| | Disintegrant | 20% of PVPP (Polyplasdone XL) |
| | | 100% |
| g. | Base component | 90% of tartaric acid, fine grit |
| | Binder | 1% of PVP K30 dissolved in 4% of alcohol |
| | Disintegrant | 9% of PVPP |
| | | 100% |
| h. | Base component | 77% of sodium carbonate |
| | Binder | 3% of PVP K30 dissolved in 7.5% of alcohol |
| | Disintegrant | 20% of rice starch |
| | | 100% |

For the purposes of the invention, the best effect is obtained using an insoluble disintegrant whose volume increases greatly with water absorption, in particular starch and crosslinked polyvinylpolypyrrolidone. Avicel (microcelllose) absorbs water and acts as the tabletting assistant but increases its volume only minimally, if at all. Carboxymethylcellulose is a soluble disintegrant which does not promote the effect according to the invention but tends to interfere with it.

EXAMPLE 45

| |
|---|
| 200 mg of acetylcysteine |
| 120 mg of sodium carbonate |
| 144 mg of PVP/PVPP-coated tartaric acid (according to Example 44) |
| 63 mg of dry rice starch |
| 200 mg of tablettose (lactose) |
| 10 mg of saccharin Na |
| 60 mg of "cassis" aroma |
| 797 mg are compressed to give a tablet which dissolves in 50 ml of water in the course of 48 to 50 seconds. |

The weight ratio of disintegrant to reactant can be reduced mainly where the active substance itself assists in the phenomenon according to the invention, i.e. particularly, for example, in the case of ibuprofen, which is hydrophobic and water-insoluble and prevents excessively rapid reaction of the effervescent tablet. It is desirable to keep the content of disintegrant as low as possible because the disintegrant initially causes turbidity of the solution and in particular the PVPP produces unattractive residues in relatively large amounts as a result of its complete insolubility in water.

The particle sizes of the substances used can therefore be varied within wide limits because they are related to the nature of the active substance. If the active substance is, for example, water-insoluble, the particle size can be substantially smaller. If the active substance is soluble, the particle size of the reactants may be larger.

The best results are of course obtained if the reaction tablet according to the invention is compressed without a lubricant on special machines. Surprisingly, however, it is also possible to use lubricants, such as magnesium stearate or polyethylene glycol, the dissolution times, however, being slightly increased; the addition of lubricants is less noticeable here than in the case of standard effervescent tablets, in which lubricants generally dramatically increase the dissolution time.

It is possible to incorporate, for example, up to 5%, indeed even 10%, of polyethylene glycol without greatly reducing the disintegration and effervescence time. This also makes it unnecessary to use special machines for compression, and it is even possible to carry out processing in non-conditioned rooms.

We claim:

1. Uncoated, compressed tablet for the preparation of an orally applicable aqueous suspension or solution of a pharmaceutically active substance, comprising in a mixture with one another at least one pharmaceutically active substance, a disintegrant effective amount of at least one water insoluble, water swellable disintegrant which is starch or crosslinked polyvinylpolypyrrolidone and an effervescent effective amount of an effervescent system which generates a gas upon contact with water comprising a first constituent selected from the group consisting of L-tartaric acid, fumaric acid, citric acid, malic acid, monosodium citrate and adipic acid and a second constituent which is an alkali metal or alkaline earth metal carbonate or bicarbonate, wherein the weight ratio of disintegrant to said system is from 0.1:1 to 4:1.

2. Tablet according to claim 1, wherein the weight ratio of disintegrant to reactants is from 0.3 : 1 to 1 : 1.

3. Tablet according to claim 1, wherein at least one constituent dissolves more slowly in water than any one of the disintegrants absorbs water.

4. Tablet according to claim 1, wherein the disintegrants and constituents together account for 25 to 75 percent by weight of the tablet.

5. Tablet according to claim 4, wherein the disintegrants and constituents account for 33 to 60 percent by weight of the tablet.

6. Tablet according to claim 1, wherein one of the constituents is selected from the group of alkali and alkaline earth metal carbonates and bicarbonates, and wherein at least 50% of said constituent have a particle size of more than 0.05 mm.

7. Tablet according to claim 6, wherein at least 50% of said reactant have a particle size of more than 0.1 mm.

8. Tablet according to claim 1, wherein one of the constituents is L-tartaric acid of which at least 50% have a particle size of between 0.2 and 0.5 mm.

9. Tablet according to claim 1, wherein one of the reactants is fumaric acid of which at least 50% have a particle size of less than 0.1 mm.

10. Tablet according to claim 1, wherein one of the reactants is citric acid of which at least 50% have a particle size of more than 0.3 mm.

11. Tablet according to claim 1, wherein one of the constituents is selected from the group of monosodium citrate and adipic acid and wherein at least 50% of said constituent have a particle size of 0.05 to 0.2 mm.

12. Tablet according to claim 1, wherein the particles of at least one constituent are coated with a slowly soluble, physiologically acceptable substance.

13. Tablet according to claim 12, wherein said slowly soluble substance is selected from long-chain polyvinylpyrrolidone and polyethylene glycol.

14. Tablet according to claim 1, wherein said disintegrant is selected from the group of crosslinked polyvinylpolypyrrolidone and starch.

15. Tablet according to claim 14, wherein crosslinked polyvinylpolypyrrolidone and starch are both present in a ratio of from 1 : 0.25 to 1 : 3.0.

16. Tablet according to claim 1, wherein said disintegrant is coated with 1 to 20 percent by weight of a physiologically acceptable compound being soluble in a solvent which does not swell the disintegrant.

17. Tablet according to claim 16, wherein said disintegrant is coated with 3 to 10 percent by weight of said physiologically acceptable compound.

18. Tablet according to claim 16, wherein said compound is selected from the group of edible organic acids and long chain non-crosslinked polyvinylpyrrolidone.

19. Tablet according to claim 1, wherein said disintegrant is anchored to the surface of the particles of at least one of the constituents.

20. Tablet according to claim 17, wherein said compound is selected from the group of edible organic acids and long-chain non-crosslinked polyvinylpyrrolidone.

21. Tablet according to claim 16, wherein said disintegrant is anchored to the surface of the particles of at least one of the reactants.

22. Tablet according to claim 1 wherein the constituents of the effervescent system and the disintegrants are such that the reaction of the effervescent system constituents to generate a gas upon contact with water occurs more slowly than the rate of water absorption by the disintegrant.

* * * * *